US012658314B2

(12) United States Patent
Cho

(10) Patent No.: US 12,658,314 B2
(45) Date of Patent: Jun. 16, 2026

(54) SYSTEM AND METHOD FOR MANAGING HOSPITAL SURGICAL INSTRUMENTS

(71) Applicant: Shin Hwan Cho, Osan-si (KR)

(72) Inventor: Shin Hwan Cho, Osan-si (KR)

( * ) Notice: Subject to any disclaimer, the term of this patent is extended or adjusted under 35 U.S.C. 154(b) by 82 days.

(21) Appl. No.: 18/862,520

(22) PCT Filed: May 3, 2023

(86) PCT No.: PCT/KR2023/005998
§ 371 (c)(1),
(2) Date: Nov. 1, 2024

(87) PCT Pub. No.: WO2023/214779
PCT Pub. Date: Nov. 9, 2023

(65) Prior Publication Data
US 2025/0285748 A1 Sep. 11, 2025

(30) Foreign Application Priority Data

May 3, 2022 (KR) ........................ 10-2022-0054902

(51) Int. Cl.
G16H 40/40 (2018.01)
(52) U.S. Cl.
CPC ................................... G16H 40/40 (2018.01)
(58) Field of Classification Search
CPC .................................................. G16H 40/40
See application file for complete search history.

(56) References Cited

U.S. PATENT DOCUMENTS

| | | | |
|---|---|---|---|
| 2013/0018666 A1* | 1/2013 | Murphy | ................. A61B 17/58 |
| | | | 705/2 |
| 2014/0172446 A1* | 6/2014 | Dumouchel | ........... A61B 90/96 |
| | | | 705/2 |
| 2016/0371639 A1 | 12/2016 | Smith et al. | |
| 2019/0206556 A1* | 7/2019 | Shelton, IV | ..... G06Q 10/06315 |

(Continued)

FOREIGN PATENT DOCUMENTS

| | | |
|---|---|---|
| JP | 2006-318038 A | 11/2006 |
| KR | 10-2003-0088605 A | 11/2003 |

(Continued)

OTHER PUBLICATIONS

International Search Report for PCT/KR2023/005998 mailed Aug. 4, 2023 from Korean Intellectual Property Office.

(Continued)

*Primary Examiner* — Karen A Hranek
*Assistant Examiner* — David Choi
(74) *Attorney, Agent, or Firm* — Revolution IP, PLLC

(57) ABSTRACT

The present invention relates to a system and method for managing hospital surgical instruments, wherein the system for managing hospital surgical instruments, according to the present invention, can automatically manage all histories of surgical instruments used in a hospital wherein the surgical instruments are stored in a hospital storage room, the surgical instruments and the quantity thereof are checked before the release thereof is prepared according to surgical instrument request information, the release of the surgical instruments is on standby, and the surgical instruments are released to a hospital department or operating room and used for surgery.

6 Claims, 3 Drawing Sheets

(56)     References Cited

U.S. PATENT DOCUMENTS

| | | | |
|---|---|---|---|
| 2020/0143195 A1 | 5/2020 | Montano | |
| 2021/0236227 A1* | 8/2021 | Kumar | A61B 90/08 |

FOREIGN PATENT DOCUMENTS

| | | | | |
|---|---|---|---|---|
| KR | 10-2011-0111977 A | 10/2011 | | |
| KR | 10-2014-0127534 A | 11/2014 | | |
| KR | 10-2016-0116949 A | 10/2016 | | |
| KR | 10-1886172 B1 | 9/2018 | | |
| KR | 20210011106 A * | 2/2021 | | A61L 2/24 |
| WO | 95/27252 A1 | 10/1995 | | |

OTHER PUBLICATIONS

European search report of European Patent Application No. 23799660.8 mailed Apr. 9, 2026.

* cited by examiner

FIG.3

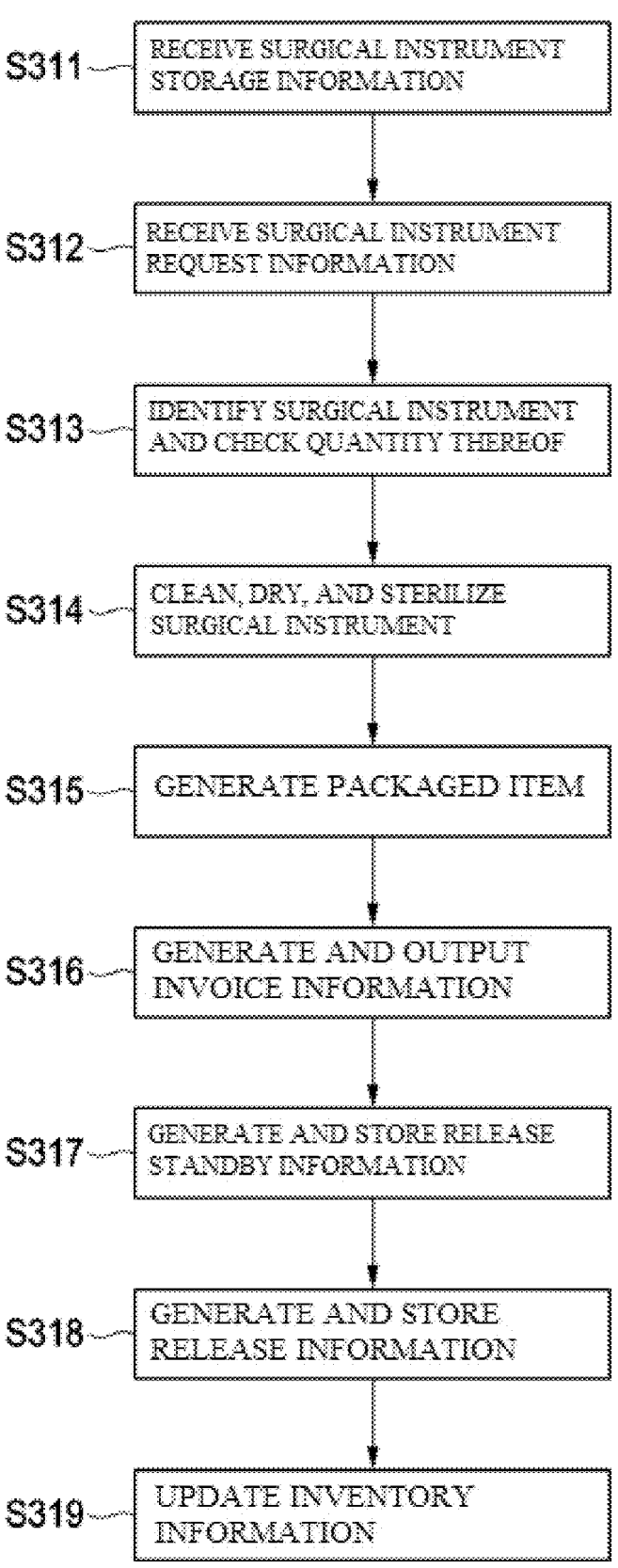

S311 — RECEIVE SURGICAL INSTRUMENT STORAGE INFORMATION

S312 — RECEIVE SURGICAL INSTRUMENT REQUEST INFORMATION

S313 — IDENTIFY SURGICAL INSTRUMENT AND CHECK QUANTITY THEREOF

S314 — CLEAN, DRY, AND STERILIZE SURGICAL INSTRUMENT

S315 — GENERATE PACKAGED ITEM

S316 — GENERATE AND OUTPUT INVOICE INFORMATION

S317 — GENERATE AND STORE RELEASE STANDBY INFORMATION

S318 — GENERATE AND STORE RELEASE INFORMATION

S319 — UPDATE INVENTORY INFORMATION

SYSTEM AND METHOD FOR MANAGING HOSPITAL SURGICAL INSTRUMENTS

CROSS REFERENCE TO PRIOR APPLICATIONS

This application is a National Stage Application of PCT International Patent Application No. PCT/KR2023/005998 filed on May 3, 2023, under 35 U.S.C. § 371, which claims priority to Korean Patent Application No. 10-2022-0054902 filed on May 3, 2022, which are all hereby incorporated by reference in their entirety.

TECHNICAL FIELD

The present invention relates to a system for managing hospital surgical instruments and an operation method thereof, and more particularly, to a system and method for managing hospital surgical instruments that automatically manage all histories of surgical instruments used in a hospital, including those being stored in a storage room, released out, and used for surgery.

BACKGROUND ART

Surgery is an act of incising, cutting, and suturing human tissue using surgical instruments. In a medical system, instruments used by doctors for surgery are typically prescribed by hand by staff members, and the manually prescribed surgical instruments are prepared by nurses before surgery. However, in a medical system where surgical instruments are prescribed by hand, there is a problem that mistakes or omissions can easily occur during a process of preparing surgical instruments by medical staff. When surgical instrument sets are not prepared properly, surgery may be delayed, or various problems may occur during the surgical process due to the omission of surgical instruments.

Accordingly, currently, electronic medical record (EMR) systems are being built to comprehensively manage medical records previously recorded on paper documents by storing the medical records in computer media, mainly in general hospitals and university hospitals, and after surgery is completed, instruments used in the surgery are input into a computer and recorded in the EMR system. In relation to this, "SURGERY INFORMATION MANAGEMENT APPARATUS AND METHOD BASED ON EMR SYSTEM" is disclosed in Korean Laid-open Patent Publication No. 10-2014-0127534.

In conventional EMR systems including Korean Laid-open Patent Publication No. 10-2014-0127534, a selection window or check box for selecting surgical instruments is formed in a window for recording medical records, and after surgery is completed, medical staff selects the surgical instruments that have been used in the surgery through the selection window or check box using a computer mouse or keyboard so that the selected surgical instruments are stored in the EMR system. However, since the types of instruments used in surgery vary widely depending on the type of surgery and procedure, a process of selecting the instruments that have been used in surgery through a selection window or checkbox takes a long time and there is a problem that errors or omissions in surgical instruments can easily occur.

In particular, surgical operations require the preparation of both a main set of surgical instruments and additional sets of different surgical instruments depending on the location of the lesion, and after the surgical operation, the surgical instruments that have been used in the actual operation are organized and recorded firstly by hand and then stored in the EMR system. However, since the types of surgical instruments that have been used in surgical operations are diverse, problems of errors or omissions in surgical instruments occur more frequently. As described above, the EMR systems currently and mainly built in general hospitals and university hospitals have the problems of errors or omissions in surgical instruments, and in the case where errors or omissions in surgical instruments occur, the cost is not properly reflected even when expensive surgical instruments are used, and thus general hospitals and university hospitals have no choice but to bear the resulting losses.

DISCLOSURE

Technical Problem

The present invention is directed to providing a system and method for managing hospital surgical instruments that automatically manage all histories of surgical instruments used in a hospital, including those being stored in a storage room, released out, and used for surgery.

Technical Solution

One aspect of the present invention provides a system for managing hospital surgical instruments which includes:

a storage processing unit configured to, when identification information, name, and quantity of surgical instruments to be stored in a warehouse in a hospital are input, generate surgical instrument storage information including the identification information, name, and quantity of the surgical instruments and an input date and time, and store the generated surgical instrument storage information in a storage unit;

surgical instrument request processing unit configured to receive surgical instrument request information including name and quantity of surgical instruments and medical staff information that are transmitted from a department terminal or operating room terminal of the hospital, store the received surgical instrument request information in the storage unit, generate a message that allows an administrator to recognize that new surgical instrument request information has arrived, and output the generated message to a display unit;

a surgical instrument recognition processing unit configured to extract an image consisting only of the identification information of the surgical instruments from an image of an entire area of a tray on which a plurality of surgical instruments are placed, captured by a first camera, identify the identification information of each surgical instrument from the extracted image consisting only of the identification information of the surgical instruments, detect the name of the surgical instrument corresponding to the identification information of each surgical instrument from the storage unit, then calculate the quantity of the surgical instruments placed on the tray using the number of pieces of identified identification information of the surgical instruments, determine whether the detected name and quantity of the surgical instruments match the name and quantity of the surgical instruments included in the surgical instrument request information, and output a result of the determination to an audio output unit or the display unit;

a surgical instrument cleaning unit configured to firstly clean the surgical instruments immersed in a cleaning solution or distilled water with ultrasonic waves, immerse the surgical instruments that have been firstly cleaned in ultrapure water, then clean the surgical instruments secondarily using nitrogen, and dry and sterilize the surgical instruments that have been secondarily cleaned;

a surgical instrument packaging unit configured to package the surgical instruments that have been cleaned, dried, and sterilized in the surgical instrument cleaning unit, and make a single packaged item;

an invoice processing unit configured to generate invoice information that allows a person to identify the packaged item, and output the generated invoice information to a printer;

a release standby processing unit configured to generate release standby information including an image of the packaged item to which the invoice information is attached, captured by a second camera, and the invoice information generated in the invoice processing unit, and then store the generated release standby information in the storage unit;

a release processing unit configured to, when information obtained by scanning the invoice information attached to the packaged item on standby to be released is input, generate surgical instrument release information including a release date and time, and the name and quantity of the surgical instruments included in the packaged item, and then store the generated surgical instrument release information in the storage unit; and an inventory information processing unit configured to calculate the type and quantity of surgical instruments currently remaining using the surgical instrument storage information and surgical instrument release information that are stored in the storage unit, generate inventory information, and then store the generated inventory information in the storage unit.

Further, the surgical instrument request information may further include additional information indicating whether the surgical instrument request information is emergency request information or general request information, and the surgical instrument request processing unit may check the additional information included in the surgical instrument request information, and when the corresponding surgical instrument request information is emergency request information, additionally output an emergency alarm message that allows the administrator to recognize that the emergency surgical instrument request information has arrived.

Further, the invoice processing unit may convert the surgical instrument release information including information on a hospital department or operating room that requested the surgical instruments, the name and quantity of the surgical instruments, and a release date and time into a label sticker output format and output the converted label sticker output format to the printer.

Another aspect of the present invention provides a method of managing hospital surgical instruments, which includes:

receiving surgical instrument storage information including identification information, name, and quantity of surgical instruments to be stored in a warehouse in a hospital and an input date and time and storing the generated surgical instrument storage information;

receiving surgical instrument request information including name and quantity of surgical instruments and medical staff information that are transmitted from a department terminal or operating room terminal of a hospital, storing the received surgical instrument request information in a storage unit, generating a message that allows an administrator to recognize that new surgical instrument request information has arrived, and outputting the generated message;

extracting an image consisting only of the identification information of the surgical instruments from an image of an entire area of a tray on which a plurality of surgical instruments are placed, captured by a first camera, then identifying the identification information of each surgical instrument from the extracted image consisting only of the identification information of the surgical instruments, detecting the name of the surgical instrument corresponding to the identification information of each surgical instrument from the storage unit, and then calculating the quantity of the surgical instruments placed on the tray using the number of pieces of identified identification information of the surgical instruments;

determining whether the detected name and quantity of the surgical instruments match the name and quantity of the surgical instruments included in the surgical instrument request information, and outputting a result of the determination through sound or to a screen;

firstly cleaning surgical instruments immersed in a cleaning solution or distilled water with ultrasonic waves, immersing the surgical instruments that have been firstly cleaned in ultrapure water, then cleaning the surgical instruments secondarily using nitrogen, and drying and sterilizing the surgical instruments that have been secondarily cleaned;

packaging the surgical instruments that have been cleaned, dried, and sterilized and making a single packaged item;

generating invoice information that allows a person to identify the packaged item and outputting the generated invoice information to a printer;

generating release standby information including an image of the packaged item to which the invoice information is attached, captured by a second camera, and the invoice information generated in the invoice processing unit, and then storing the generated release standby information in the storage unit;

when information obtained by scanning the invoice information attached to a packaged item on standby to be released is input, generating surgical instrument release information including a release date and time, and the name and quantity of the surgical instruments included in the packaged item, and then storing the generated surgical instrument release information in the storage unit; and calculating the type and quantity of surgical instruments currently remaining using the surgical instrument storage information and surgical instrument release information that are stored in the storage unit, generating inventory information, and then storing the generated inventory information in the storage unit.

Further, the receiving of the surgical instrument request information including the name and quantity of the surgical instruments and the medical staff information that are transmitted from the department terminal or operating room terminal of the hospital, storing the received surgical instrument request information in the storage unit, generating the message that allows the administrator to recognize that the new surgical instrument request information has arrived, and outputting the generated message may further include checking additional information included in the surgical instrument request information, and when the corresponding surgical instrument request information is emergency request information, outputting an emergency alarm message that allows the administrator to recognize that the emergency surgical instrument request information has arrived.

Further, the generating of the invoice information that allows the person to identify the packaged item and outputting the generated invoice information to the printer may include converting the surgical instrument release information including information on a hospital department or operating room that requested the surgical instruments, and the name and quantity of the surgical instruments, and a release date and time into a label sticker output format and outputting the converted label sticker output format to the printer.

Still another aspect of the present invention provides a system for managing hospital surgical instruments which includes:

a storage processing unit configured to generate surgical instrument storage information including identification information, name, and quantity of surgical instruments to be stored in a hospital, and an input date and time and store the generated surgical instrument storage information in a storage unit;

a surgical instrument request processing unit configured to receive surgical instrument request information including name and quantity of surgical instruments and medical staff information that are transmitted from a department terminal or operating room terminal of the hospital, store the received surgical instrument request information in the storage unit, generate a message that allows an administrator to recognize that new surgical instrument request information has arrived, and output the generated message to a display unit;

a surgical instrument recognition processing unit configured to extract an image consisting only of the identification information of the surgical instruments from an image of an entire area of a tray on which a plurality of surgical instruments are placed, captured by a first camera, identify the identification information of each surgical instrument from the extracted image consisting only of the identification information of the surgical instruments, detect the name of the surgical instrument corresponding to the identification information of each surgical instrument from the storage unit, then calculate the quantity of the surgical instruments placed on the tray using the number of pieces of identified identification information of the surgical instruments, determine whether the detected name and quantity of the surgical instruments match the name and quantity of the surgical instruments included in the surgical instrument request information, and output a result of the determination to an audio output unit or the display unit;

a surgical instrument cleaning unit configured to store a result of the cleaning of the surgical instruments;

a surgical instrument packaging unit configured to store a result of the packaging of the surgical instruments;

an invoice processing unit configured to generate invoice information that allows a person to identify a packaged item, and output the generated invoice information to a printer;

a release standby processing unit configured to generate release standby information including an image of the packaged item to which the invoice information is attached, captured by a second camera, and the invoice information generated in the invoice processing unit, and then store the generated release standby information in the storage unit;

a release processing unit configured to, when information obtained by scanning the invoice information attached to the packaged item on standby to be released is input, generate surgical instrument release information including a release date and time, and the name and quantity of the surgical instruments included in the packaged item, and then store the generated surgical instrument release information in the storage unit; and an inventory information processing unit configured to calculate the type and quantity of surgical instruments currently remaining using the surgical instrument storage information and surgical instrument release information that are stored in the storage unit, generate inventory information, and then store the generated inventory information in the storage unit.

Further, the surgical instrument request information may further include additional information indicating whether the surgical instrument request information is emergency request information or general request information, and the surgical instrument request processing unit may check the additional information included in the surgical instrument request information, and when the corresponding surgical instrument request information is emergency request information, additionally output an emergency alarm message that allows the administrator to recognize that the emergency surgical instrument request information has arrived.

Further, the invoice processing unit may convert the surgical instrument release information including information on a hospital department or operating room that requested the surgical instruments, the name and quantity of the surgical instruments, and a release date and time into a label sticker output format and output the converted label sticker output format to the printer.

Yet another aspect of the present invention provides a method of managing hospital surgical instruments which includes:

receiving surgical instrument storage information including identification information, name, and quantity of surgical instruments to be stored in a hospital, and an input date and time and storing the generated surgical instrument storage information;

receiving surgical instrument request information including name and quantity of surgical instruments and medical staff information that are transmitted from a department terminal or operating room terminal of a hospital, storing the received surgical instrument request information in a storage unit, generating a message that allows an administrator to recognize that new surgical instrument request information has arrived, and outputting the generated message;

extracting an image consisting only of the identification information of the surgical instruments from an image of an entire area of a tray on which a plurality of surgical instruments are placed, captured by a first camera, then identifying the identification information of each surgical instrument from the extracted image consisting only of the identification information of the surgical instruments, detecting the name of the surgical instrument corresponding to the identification information of each surgical instrument from the storage unit, and then calculating the quantity of the surgical instruments placed on the tray using the number of pieces of identified identification information of the surgical instruments;

determining whether the detected name and quantity of the surgical instruments match the name and quantity of the surgical instruments included in the surgical instrument request information, and outputting a result of the determination through sound or to a screen;

storing a result of the cleaning of the surgical instrument;

storing a result of the packaging of the surgical instrument;

generating invoice information that allows a person to identify a packaged item, and outputting the generated invoice information to a printer;

generating release standby information including an image of the packaged item to which the invoice information is attached, captured by a second camera, and the invoice information generated in the invoice processing unit, and then storing the generated release standby information in the storage unit;

when information obtained by scanning the invoice information attached to a packaged item on standby to be released is input, generating surgical instrument release information including a release date and time, and the name and quantity of the surgical instruments included in the packaged item, and then storing the generated surgical instrument release information in the storage unit; and calculating the type and quantity of surgical instruments currently remaining using the surgical instrument storage information and surgical instrument release information that are stored in the storage unit, generating inventory information, and then storing the generated inventory information in the storage unit.

Further, the receiving of the surgical instrument request information including the name and quantity of the surgical instruments and the medical staff information that are transmitted from the department terminal or operating room terminal of the hospital, storing the received surgical instrument request information in the storage unit, generating the message that allows the administrator to recognize that the new surgical instrument request information has arrived, and outputting the generated message may further include checking additional information included in the surgical instrument request information, and when the corresponding surgical instrument request information is emergency request information, outputting an emergency alarm message that allows the administrator to recognize that the emergency surgical instrument request information has arrived.

Further, the generating of the invoice information that allows the person to identify the packaged item and outputting the generated invoice information to the printer may include converting the surgical instrument release information including information on a hospital department or operating room that requested the surgical instruments, and the name and quantity of the surgical instruments, and a release date and time into a label sticker output format and outputting the converted label sticker output format to the printer.

Yet another aspect of the present invention provides a system for managing hospital surgical instruments which includes:

a storage processing unit configured to generate surgical instrument storage information including identification information, name, and quantity of surgical instruments to be stored in a hospital, and an input date and time and store the generated surgical instrument storage information in a storage unit;

a surgical instrument request processing unit configured to receive surgical instrument request information including name and quantity of surgical instruments and medical staff information that are transmitted from a department terminal or operating room terminal of the hospital, store the received surgical instrument request information in the storage unit, generate a message that allows an administrator to recognize that new surgical instrument request information has arrived, and output the generated message to a display unit;

a surgical instrument recognition processing unit configured to extract an image consisting only of the identification information of the surgical instruments from an image of an entire area of a tray on which a plurality of surgical instruments are placed, captured by a first camera, identify each surgical instrument, and output a result of the identification to an audio output unit or a display unit;

a surgical instrument packaging unit configured to store a result of the packaging of the surgical instruments;

an invoice processing unit configured to generate invoice information that allows a person to identify a packaged item, and output the generated invoice information to a printer;

a release standby processing unit configured to generate release standby information including an image of the packaged item captured by a second camera, and the invoice information generated in the invoice processing unit, and then store the generated release standby information in the storage unit;

a release processing unit configured to, when information obtained by scanning the invoice information attached to the packaged item on standby to be released is input, generate surgical instrument release information including a release date and time, and the name and quantity of the surgical instruments included in the packaged item, and then store the generated surgical instrument release information in the storage unit; and an inventory information processing unit configured to calculate the type and quantity of surgical instruments currently remaining using the surgical instrument storage information and surgical instrument release information that are stored in the storage unit, generate inventory information, and then store the generated inventory information in the storage unit.

Yet another aspect of the present invention provides a method of managing hospital surgical instruments which includes:

receiving surgical instrument storage information including identification information, name, and quantity of surgical instruments to be stored in a hospital, and an input date and time and storing the generated surgical instrument storage information;

receiving surgical instrument request information including name and quantity of surgical instruments and medical staff information that are transmitted from a department terminal or operating room terminal of a hospital, storing the received surgical instrument request information in a storage unit, generating a message that allows an administrator to recognize that new surgical instrument request information has arrived, and outputting the generated message;

extracting an image consisting only of the identification information of the surgical instruments from an image of an entire area of a tray on which a plurality of surgical instruments are placed, captured by a first camera, identifying each surgical instrument, and out-
putting a result of the identification to an audio output
unit or a display unit;

storing a result of the cleaning of the surgical instrument;

storing a result of the packaging of the surgical instru-
ment;

generating invoice information that allows a person to
identify a packaged item, and outputting the generated
invoice information to a printer;

generating release standby information including an
image of the packaged item captured by a second
camera, and the invoice information generated in the
invoice processing unit, and then storing the generated
release standby information in the storage unit;

when information obtained by scanning the invoice infor-
mation attached to a packaged item on standby to be
released is input, generating surgical instrument release
information including a release date and time, and the
name and quantity of the surgical instruments included
in the packaged item, and then storing the generated
surgical instrument release information in the storage
unit; and calculating the type and quantity of surgical instruments
currently remaining using the surgical instrument stor-
age information and surgical instrument release infor-
mation that are stored in the storage unit, generating
inventory information, and then storing the generated
inventory information in the storage unit.

Advantageous Effects

According to the present invention, it is possible to
automatically manage all histories of surgical instruments
used in a hospital wherein the surgical instruments are stored
in a hospital storage room, the surgical instruments and the
quantity thereof are checked before the release thereof is
prepared according to surgical instrument request informa-
tion, the release of the surgical instruments is on standby,
and the surgical instruments are released to a hospital
department or operating room and used for surgery.

DESCRIPTION OF DRAWINGS

FIG. 3 is a flowchart of a method of managing hospital
surgical instruments according to the present invention.

BEST MODE OF THE INVENTION

Figure 1:
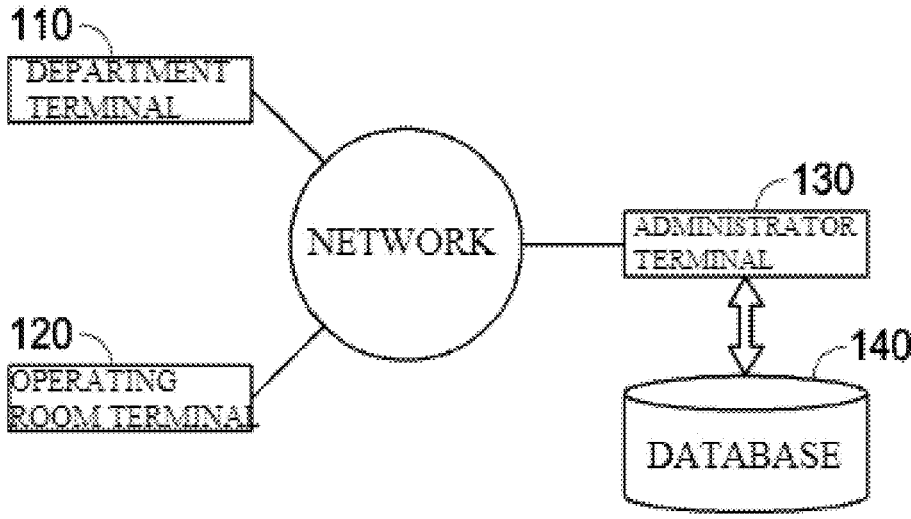
FIG. 1 is an exemplary diagram for describing an entire
system according to the present invention.

Advantages and features of the present invention and
methods of achieving the same will be clearly understood
with reference to the accompanying drawings and embodi-
ments described in detail below. However, the present
invention is not limited to the embodiments to be disclosed
below but may be implemented in various different forms.
The embodiments are provided in order to fully explain the
present embodiments and fully explain the scope of the
present invention for those skilled in the art. The scope of the
present invention is only defined by the appended claims.
Like reference numerals refer to like elements throughout
the specification.

The terminology used herein is for the purpose of describ-
ing particular embodiments only and is not intended to be limiting to the present invention. As used herein, the singular
forms "a" and "an" are intended to also include the plural
forms, unless the context clearly indicates otherwise. It
should be further understood that the terms "comprise,"
"comprising," "include," and/or "including" when used
herein specify the presence of stated features, integers, steps,
operations, elements, parts, or combinations thereof, but do
not preclude the presence or addition of one or more other
features, integers, steps, operations, elements, parts, or com-
binations thereof.

Figure 2:
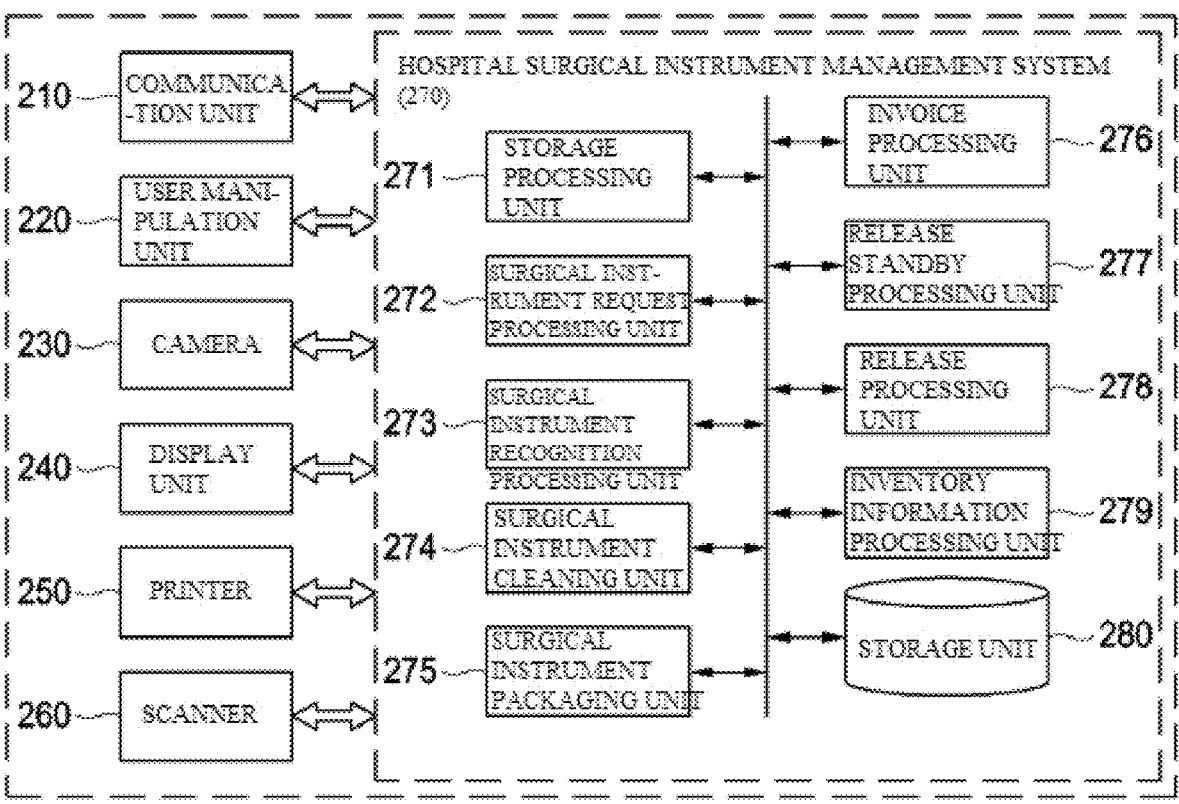
FIG. 2 is an exemplary diagram for describing a configu-
ration of a system for managing hospital surgical instru-
ments according to the present invention.

FIG. 1 is an exemplary diagram for describing an entire
system according to the present invention, and FIG. 2 is an
exemplary diagram for describing a configuration of a
system for managing hospital surgical instruments accord-
ing to the present invention.

The entire system according to the present invention may
include a department terminal 110, an operating room ter-
minal 120, an administrator terminal 130 that is connected
to the department terminal 110 and the operating room
terminal 120 via a network, and a database 140, as illustrated
in FIG. 1.

The department terminal 110 is a terminal used by hos-
pital medical staff, and is a terminal used to store medical
records in departments within the hospital, such as internal
medicine, surgery, otolaryngology, orthopedics, etc. The
department terminal 110 may be implemented as a tablet
computer, a notebook computer, or a desktop computer. The
department terminal 110 may be equipped with an electronic
medical record (EMR) system.

The department terminal 110 may generate surgical
instrument request information including the name and
quantity of surgical instruments, information on the depart-
ment using the surgical instruments, and information on
medical staff, and transmit the generated surgical instrument
request information to the administrator terminal 130. For
example, the surgical instrument request information may
further include additional information indicating whether
the surgical instrument request information is emergency
request information or general request information.

The operating room terminal 120 is a terminal used by
hospital medical staff in an operating room, and may be
implemented as, for example, a tablet computer, a notebook
computer, or a desktop computer. The operating room ter-
minal 120 may be equipped with an EMR system. The
operating room terminal 120 may generate surgical instru-
ment request information including the name and quantity of
the surgical instruments, information on medical staff, and
information on the operating room, and transmit the gener-
ated surgical instrument request information to the admin-
istrator terminal 130. The surgical instrument request infor-
mation transmitted from the operating room terminal 120
includes additional information automatically checked due
to an emergency request.

The administrator terminal 130 is a terminal used by a
department that manages medical supplies (e.g., hospital
gowns, surgical instruments, etc.) including surgical instru-
ments that are stored and released within the hospital, may
be implemented as a tablet computer, a notebook computer,
or a desktop computer, and may be equipped with an EMR
system. In particular, the administrator terminal 130 man-
ages the storage, release, and inventory of surgical instru-
ments, and manages usage history of surgical instruments in
the operating room.

The database 140 may be implemented as a network
server or a server within a data center. The database 140
stores information used in an EMR system that includes
information on storage and release of medical supplies (e.g., hospital gowns, surgical instruments, etc.) and inventory information. In this specification, only surgical instrument storage information, surgical instrument release information, and inventory information will be described.

Surgical instrument storage information includes identification information, name, and quantity of surgical instruments, and an input date and time. For example, the surgical instrument storage information may further include information on stores that sell the surgical instruments. Further, the surgical instrument storage information may further include images of the surgical instruments and user manuals.

Surgical instrument release information may include the name and quantity of surgical instruments, information on a hospital department or operating room that requested the surgical instruments, and a release date and time. Surgical instrument usage history information may include images of the surgical instruments used in surgery, identification information of the surgical instruments, and information on medical staff who performed the surgery. Surgical instrument inventory information includes the current inventory quantity of each surgical instrument remaining.

Hereinafter, a hospital surgical instrument management system 270 according to the present invention will be described with reference to FIG. 2. The hospital surgical instrument management system 270 according to the present invention may include peripheral devices such as a communication unit 210, a user manipulation unit 220, a camera 230, a display unit 240, a printer 250, and a scanner 260. The hospital surgical instrument management system 270 may be configured to be separate from an EMR system or may be configured to be integrated with the EMR system. The hospital surgical instrument management system 270 may be configured to be controlled by the administrator terminal of FIG. 1.

The communication unit 210 is a terminal or server capable of transmitting or receiving data packets through a circuit switched network (CSN) and a packet switched network (PSN), and may be implemented as a modem for communication such as code division multiple access (CDMA), time division multiple access (TDMA), wide code division multiple access (WCDMA), Global System for Mobile Communications (GSM), Long-Term Evolution (LTE), etc., or may be implemented as a communication module capable of short-distance wireless communication such as Wi-Fi and Bluetooth, and wired Internet.

The user manipulation unit 220 generates input data according to a user's manipulation command. The user manipulation unit 220 may be a peripheral device such as a voice recognition device, a touch pad, a mouse, a keyboard, etc. The camera 230 may include a lens module and an image sensor that processes image signals. The camera 230 uses a wide-angle lens that can photograph an entire area of a tray on which surgical instruments are placed for storage or release.

The display unit 240 is implemented as a display such as a liquid-crystal display (LCD) and a light-emitting diode (LED). The display unit 240 may be implemented as a display device such as a television (TV) monitor or a smart board as well as a conventional computer monitor. The printer 250 uses a label sticker as paper and prints output information generated in the hospital surgical instrument management system 270, such as surgical instrument release information including the name, release date, quantity, and release location of the surgical instrument, on the label sticker. The scanner 260 reads invoice information printed on the label sticker.

The hospital surgical instrument management system 270 may be implemented as a combination of physical hardware such as a read only memory (ROM) in which an execution program is stored, a random access memory (RAM) in which data is stored, an interface module that processes serial communication, parallel communication, and Inter-Integrated Circuit (I2C) signals, and a processor as an integral part. The hospital surgical instrument management system 270 may largely include a storage processing unit 271, a surgical instrument request processing unit 272, a surgical instrument recognition processing unit 273, a surgical instrument cleaning unit 274, a surgical instrument packaging unit 275, an invoice processing unit 276, a release standby processing unit 277, a release processing unit 278, an inventory information processing unit 279, and a storage unit 280, as illustrated in FIG. 2.

When identification information, name, and quantity of surgical instruments to be stored in a warehouse of a hospital are input according to an administrator's manipulation and input, the storage processing unit 271 generates surgical instrument storage information including the identification information, name, and quantity of the surgical instruments and an input date and time and stores the generated surgical instrument storage information in the storage unit 280. Examples of the surgical instruments include various instruments, such as forceps, scissors, forceps, scalpel handles, swabs, scalpels, tongue depressors, etc. The identification information of the surgical instrument is implemented as characters or a series of numbers, and is unique identification information that is printed at a specific location of the surgical instrument using a laser marking method and used to identify the surgical instrument. The identification information of the surgical instrument may be implemented not only at a specific location but also in a unique shape such as a semi-circular or elliptical shape.

The surgical instrument request processing unit 272 receives surgical instrument request information including name and quantity of the surgical instruments and medical staff information that are transmitted from the department terminal 110 or operating room terminal 120 in the hospital, stores the received surgical instrument request information in the storage unit, generates a message that allows the administrator to recognize that new surgical instrument request information has arrived, and outputs the generated message to the display unit 240.

For example, the surgical instrument request information may further include additional information indicating whether the surgical instrument request information is emergency request information or general request information. According to this embodiment, the surgical instrument request processing unit 272 may check the additional information included in the surgical instrument request information, and when the corresponding surgical instrument request information is emergency request information, additionally output an emergency alarm message that allows the administrator to recognize that the emergency surgical instrument request information has arrived.

The administrator divides a plurality of pieces of surgical instrument request information into emergency request information and general request information, checks the name and quantity of the surgical instruments included in the surgical instrument request information which is the emergency request information, finds the corresponding surgical instruments in the warehouse of the hospital, and places the found surgical instruments on a tray. Although a person can directly check the surgical instruments and the quantity thereof, the hospital surgical instrument management system 270 according to the present invention is implemented to check the surgical instruments and the quantity thereof using an image processing technique to prevent even a single mistake or error and to perform the check rapidly.

The surgical instrument recognition processing unit 273 extracts an image consisting only of the identification information of the surgical instruments from an image of an entire area of a tray on which a plurality of surgical instruments are placed, captured by a camera, identifies the identification information of each surgical instrument from the extracted image consisting only of the identification information of the surgical instrument, and detects the name of the surgical instrument corresponding to the identification information of each surgical instrument from the storage unit 280 (note: this may be integrated into the database 140 of FIG. 1). The surgical instrument recognition processing unit 273 calculates the quantity of the surgical instruments placed on the tray using the number of pieces of identified identification information of the surgical instruments. The surgical instrument recognition processing unit 273 determines whether the detected name and quantity of the surgical instruments match the name and quantity of the surgical instruments included in the surgical instrument request information, and outputs a result of the determination to an audio output unit or the display unit 240.

The surgical instrument cleaning unit 274 stores information on a result of cleaning of the surgical instruments in the storage unit 280. The cleaning of the surgical instruments is performed by firstly cleaning the surgical instruments immersed in a cleaning solution or distilled water with ultrasonic waves by hand or using a predetermined cleaning device, immersing the surgical instruments that have been firstly cleaned in ultrapure water, then cleaning the surgical instruments secondarily using nitrogen, and drying and sterilizing the surgical instruments that have been secondarily cleaned. The surgical instrument cleaning unit 274 may include a cleaning device to directly perform the cleaning, drying, or sterilization process.

The surgical instrument packaging unit 275 stores information on a result of packaging of the surgical instruments in the storage unit 280. The packaging of the surgical instruments involves packaging the surgical instruments that have been cleaned, dried, and sterilized by hand or using a predetermined packaging device into a single packaged item, and may be performed using a packaging machine that packages boxes or plastic bags. The surgical instrument packaging unit 275 may include a packaging device to directly perform the packaging process.

The invoice processing unit 276 generates invoice information that allows a person to identify the packaged item according to the administrator's manipulation and input, and outputs the generated invoice information to the printer 250. The invoice information may include the name and quantity of the surgical instruments and information on a hospital department or operating room that requested the surgical instruments. For example, the invoice processing unit may convert the surgical instrument release information including the information on the hospital department or operating room that requested the surgical instruments, and the name, quantity of the surgical instruments and a release date and time into a label sticker output format and output the converted label sticker output format to the printer 250.

The release standby processing unit 277 generates release standby information including an image of the packaged item to which the invoice information is attached, captured by a camera, and the invoice information generated in the invoice processing unit 276, and then stores the generated release standby information in the storage unit 280.

When information obtained by scanning the invoice information attached to the packaged item on standby to be released using a scanner is input, the release processing unit 278 generates surgical instrument release information including the release date and time, the name and quantity of the surgical instruments included in the packaged item, and the information on the hospital department or operating room that requested the surgical instruments, and then stores the generated surgical instrument release information in the storage unit 280.

The inventory information processing unit 279 calculates the type and quantity of the surgical instruments currently remaining using the surgical instrument storage information and surgical instrument release information stored in the storage unit 280, generates inventory information, and then stores the generated inventory information in the storage unit 280.

The hospital surgical instrument management system 270 may automatically manage all histories of surgical instruments used in a hospital wherein the surgical instruments are stored in a hospital storage room, the surgical instruments and the quantity thereof are checked before the release thereof is prepared according to surgical instrument request information, the release of the surgical instruments is on standby, and the surgical instruments are released to a hospital department or operating room and used for surgery.

FIG. 3 is a flowchart of a method of managing hospital surgical instruments according to the present invention.

In operation S311, the method of managing the hospital surgical instruments according to the present invention includes receiving surgical instrument storage information including identification information, name, quantity of surgical instruments to be stored in a warehouse of a hospital and an input date and time according to an administrator's manipulation and input, and storing the received surgical instrument storage information in the storage unit. For example, the surgical instrument storage information may further include information on stores that sell the surgical instruments. Further, the surgical instrument storage information may further include images of the surgical instruments and user manuals.

Thereafter, in operation S312, the method of managing the hospital surgical instruments according to the present invention includes receiving surgical instrument request information including the name and quantity of surgical instruments and medical staff information that are transmitted from a department terminal or operating room terminal of the hospital, storing the received surgical instrument request information in the storage unit, generating a message that allows the administrator to recognize that new surgical instrument request information has arrived, and outputting the generated message.

In operation S312, for example, the surgical instrument request information may further include additional information indicating whether the surgical instrument request information is emergency request information or general request information. According to this embodiment, the method of managing the hospital surgical instruments according to the present invention may include checking the additional information included in the surgical instrument request information, and when the corresponding surgical instrument request information is emergency request information, additionally outputting an emergency alarm message that allows the administrator to recognize that the emergency surgical instrument request information has arrived.

The administrator divides a plurality of pieces of surgical instrument request information into emergency request information and general request information, checks the name and quantity of the surgical instruments included in the surgical instrument request information which is in the emergency request, finds the corresponding surgical instruments in the warehouse of the hospital, and places the found surgical instruments on a tray. Although a person can directly check the surgical instruments and the quantity thereof, the method of managing the hospital surgical instruments according to the present invention is implemented to check the surgical instruments and the quantity thereof using an image processing technique to prevent even a single mistake or error and to perform the check rapidly.

In operation S313, the method of managing the hospital surgical instruments according to the present invention includes extracting an image consisting only of the identification information of the surgical instruments from an image of an entire area of a tray on which a plurality of surgical instruments are placed, captured by a first camera, then identifying the identification information of each surgical instrument from the extracted image consisting only of the identification information of the surgical instrument, detecting the name of the surgical instrument corresponding to the identification information of each surgical instrument from the storage unit, and then calculating the quantity of the surgical instruments placed on the tray using the number of pieces of identified identification information of the surgical instruments.

Thereafter, the method of managing the hospital surgical instruments according to the present invention includes determining whether the detected name and quantity of the surgical instruments match the name and quantity of the surgical instruments included in the surgical instrument request information, and outputting a result of the determination through sound or to a screen.

In operation S314, the method of managing the hospital surgical instruments according to the present invention includes performing a process of firstly cleaning the surgical instruments immersed in a cleaning solution or distilled water with ultrasonic waves by hand or using a predetermined cleaning device, immersing the surgical instruments that have been firstly cleaned in ultrapure water, then cleaning the surgical instruments secondarily using nitrogen, drying and sterilizing the surgical instruments that have been secondarily cleaned, and storing information on a result of the performance.

In operation S315, the method of managing the hospital surgical instruments according to the present invention includes performing a process of packaging the surgical instruments that have been cleaned, dried, and sterilized by hand or using a predetermined packaging device and making a single packaged item, and storing information on a result of the performance.

In operation S316, the method of managing the hospital surgical instruments according to the present invention includes generating invoice information that allows a person to identify the packaged item according to the administrator's manipulation and input, and outputting the generated invoice information to the printer. For example, surgical instrument release information including information on a hospital department or operating room that requested the surgical instruments, the name and quantity of the surgical instruments, and a release date and time may be converted into a label sticker output format, and the converted label sticker output format may be output to the printer.

In operation S317, the method of managing the hospital surgical instruments according to the present invention includes generating release standby information including an image of the packaged item to which the invoice information is attached, captured by a second camera, and the invoice information, and then storing the generated release standby information in the storage unit.

In operation S318, the method of managing the hospital surgical instruments according to the present invention includes, when information obtained by scanning the invoice information attached to the packaged item on standby to be released is input, generating surgical instrument release information including a release date and time, and the name and quantity of the surgical instruments included in the packaged item, and then storing the generated surgical instrument release information in the storage unit.

In operation S319, the method of managing the hospital surgical instruments according to the present invention includes calculating the type and quantity of the surgical instruments currently remaining using the surgical instrument storage information and surgical instrument release information stored in the storage unit, generating inventory information, and then storing the generated inventory information in the storage unit.

While the present invention has been described with reference to several embodiments, this is intended to illustrate the present invention. Those skilled in the art may modify or changed the above embodiments in other forms while maintaining the technical idea. However, since the scope of this application is defined by the following claims, such modifications or changes may be interpreted as being included in the scope of the following claims.

The invention claimed is:

1. A system for managing hospital surgical instruments, the system comprising:

a storage processing unit, executed by a processor, configured to, when identification information, name, and quantity of surgical instruments to be stored in a warehouse in a hospital are input, generate surgical instrument storage information including the identification information, name, and quantity of the surgical instruments and an input date and time, and store the generated surgical instrument storage information in a storage unit;

a surgical instrument request processing unit, executed by the processor, configured to receive surgical instrument request information including name and quantity of surgical instruments and medical staff information that are transmitted from a department terminal or operating room terminal of the hospital, store the received surgical instrument request information in the storage unit, generate a message that allows an administrator to recognize that new surgical instrument request information has arrived, and output the generated message to a display unit;

a surgical instrument recognition processing unit, executed by the processor, configured to extract an image consisting only of the identification information of the surgical instruments from an image of an entire area of a tray on which a plurality of surgical instruments are placed, captured by a first camera, identify the identification information of each surgical instrument from the extracted image consisting only of the identification information of the surgical instruments, detect the name of the surgical instrument corresponding to the identification information of each surgical instrument from the storage unit, then calculate the quantity of the surgical instruments placed on the tray using the number of pieces of identified identification information of the surgical instruments, determine whether the detected name and quantity of the surgical instruments match the name and quantity of the surgical instruments included in the surgical instrument request information, and output a result of the determination to an audio output unit or the display unit;

a surgical instrument cleaning device that is configured to firstly clean the surgical instruments immersed in a cleaning solution or distilled water with ultrasonic waves, immerse the surgical instruments that have been firstly cleaned in ultrapure water, then clean the surgical instruments secondarily using nitrogen, and dry and sterilize the surgical instruments that have been secondarily cleaned;

a surgical instrument packaging device that is configured to package the surgical instruments that have been cleaned, dried, and sterilized in the surgical instrument cleaning unit, and make a single packaged item;

an invoice processing unit, executed by the processor, configured to generate invoice information that allows a person to identify the packaged item, and output the generated invoice information to a printer;

a release standby processing unit, executed by the processor, configured to generate release standby information including an image of the packaged item to which the invoice information is attached, captured by a second camera, and the invoice information generated in the invoice processing unit, and then store the generated release standby information in the storage unit;

a release processing unit, executed by the processor, configured to, when information obtained by scanning the invoice information attached to the packaged item on standby to be released is input, generate surgical instrument release information including a release date and time, and the name and quantity of the surgical instruments included in the packaged item, and then store the generated surgical instrument release information in the storage unit; and an inventory information processing unit, executed by the processor, configured to calculate the type and quantity of surgical instruments currently remaining using the surgical instrument storage information and surgical instrument release information that are stored in the storage unit, generate inventory information, and then store the generated inventory information in the storage unit.

2. The system of claim 1, wherein the surgical instrument request information further includes additional information indicating whether the surgical instrument request information is emergency request information or general request information, and the surgical instrument request processing unit checks the additional information included in the surgical instrument request information, and when the corresponding surgical instrument request information is emergency request information, additionally outputs an emergency alarm message that allows the administrator to recognize that the emergency surgical instrument request information has arrived.

3. The system of claim 1, wherein the invoice processing unit converts the surgical instrument release information including information on a hospital department or operating room that requested the surgical instruments, the name and quantity of the surgical instruments, and a release date and time into a label sticker output format and outputs the converted label sticker output format to the printer.

4. A method of managing hospital surgical instruments, the method comprising:

receiving surgical instrument storage information including identification information, name, and quantity of surgical instruments to be stored in a warehouse in a hospital and an input date and time and storing the generated surgical instrument storage information;

receiving surgical instrument request information including name and quantity of surgical instruments and medical staff information that are transmitted from a department terminal or operating room terminal of a hospital, storing the received surgical instrument request information in a storage unit, generating a message that allows an administrator to recognize that new surgical instrument request information has arrived, and outputting the generated message;

extracting an image consisting only of the identification information of the surgical instruments from an image of an entire area of a tray on which a plurality of surgical instruments are placed, captured by a first camera, then identifying the identification information of each surgical instrument from the extracted image consisting only of the identification information of the surgical instruments, detecting the name of the surgical instrument corresponding to the identification information of each surgical instrument from the storage unit, and then calculating the quantity of the surgical instruments placed on the tray using the number of pieces of identified identification information of the surgical instruments;

determining whether the detected name and quantity of the surgical instruments match the name and quantity of the surgical instruments included in the surgical instrument request information, and outputting a result of the determination through sound or to a screen;

firstly cleaning surgical instruments, by using a cleaning device, immersed in a cleaning solution or distilled water with ultrasonic waves, immersing the surgical instruments that have been firstly cleaned in ultrapure water, then cleaning the surgical instruments secondarily using nitrogen, and drying and sterilizing the surgical instruments that have been secondarily cleaned;

packaging the surgical instruments, by using a packaging device, that have been cleaned, dried, and sterilized and making a single packaged item; generating invoice information that allows a person to identify the packaged item and outputting the generated invoice information to a printer;

generating release standby information including an image of the packaged item to which the invoice information is attached, captured by a second camera, and the invoice information generated in the invoice processing unit, and then storing the generated release standby information in the storage unit;

when information obtained by scanning the invoice information attached to a packaged item on standby to be released is input, generating surgical instrument release information including a release date and time, and the name and quantity of the surgical instruments included in the packaged item, and then storing the generated surgical instrument release information in the storage unit; and calculating the type and quantity of surgical instruments currently remaining using the surgical instrument storage information and surgical instrument release information that are stored in the storage unit, generating inventory information, and then storing the generated inventory information in the storage unit.

5. The method of claim 4, wherein the receiving of the surgical instrument request information including the name and quantity of the surgical instruments and the medical staff information that are transmitted from the department terminal or operating room terminal of the hospital, storing the received surgical instrument request information in the storage unit, generating the message that allows the administrator to recognize that the new surgical instrument request information has arrived, and outputting the generated message further includes checking additional information included in the surgical instrument request information, and when the corresponding surgical instrument request information is emergency request information, outputting an emergency alarm message that allows the administrator to recognize that the emergency surgical instrument request information has arrived.

6. The method of claim 4, wherein the generating of the invoice information that allows the person to identify the packaged item and outputting the generated invoice information to the printer includes converting the surgical instrument release information including information on a hospital department or operating room that requested the surgical instruments, and the name and quantity of the surgical instruments, and a release date and time into a label sticker output format and outputting the converted label sticker output format to the printer.

\* \* \* \* \*